United States Patent [19]

King et al.

[11] Patent Number: 5,238,988
[45] Date of Patent: Aug. 24, 1993

[54] RAPID CURE ROOM TEMPERATURE VULCANIZABLE ORGANOSILOXANE COMPOSITIONS

[75] Inventors: Russell K. King; Chi-long Lee, both of Midland, Mich.

[73] Assignee: Dow Corning Corporation, Midland, Mich.

[21] Appl. No.: 815,790

[22] Filed: Jan. 2, 1992

[51] Int. Cl.$^5$ .................. C08K 3/26; C08K 5/3415; C08G 77/26
[52] U.S. Cl. ................................. 524/425; 524/588; 524/863; 524/788; 524/864; 528/37; 528/38; 528/18; 528/17
[58] Field of Search ............... 528/37, 38, 18, 17; 524/588, 423, 863, 788, 864

[56] References Cited
U.S. PATENT DOCUMENTS

| | | | |
|---|---|---|---|
| 3,035,016 | 5/1962 | Bruner | 260/46.5 |
| 3,077,465 | 2/1963 | Bruner | 260/46.5 |
| 3,146,250 | 8/1965 | Speier | 260/448.2 |
| 3,274,145 | 9/1966 | Dupree | 260/37 |
| 4,578,492 | 3/1986 | Pratt et al. | 556/407 |
| 5,136,064 | 8/1992 | King et al. | 556/407 |

Primary Examiner—John C. Bleutge
Assistant Examiner—Karen A. Dean
Attorney, Agent, or Firm—Roger H. Borrousch

[57] ABSTRACT

Room temperature vulcanizable silicone sealants containing acetoxy groups are fast curing. These sealants give off only small amounts of volatile materials which are generated during the curing process. These sealants contain crosslinkers and optionally chain extenders having azasilacycloalkane groups cure. The preferred azasilacycloalkanes are azasilacyclopentane groups such as

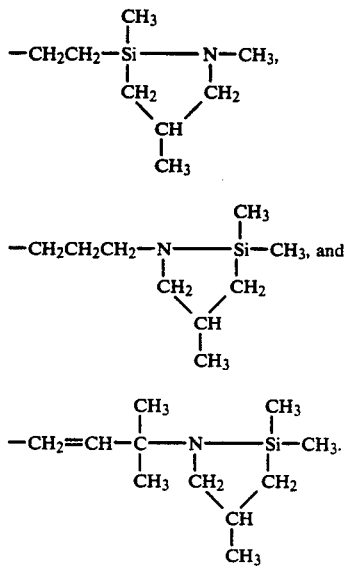

25 Claims, No Drawings

RAPID CURE ROOM TEMPERATURE VULCANIZABLE ORGANOSILOXANE COMPOSITIONS

BACKGROUND OF THE INVENTION

1. Field of the Invention

This invention relates to room temperature vulcanizable organosiloxane compositions which contain siliconbonded acetoxy groups.

2. Background Information

Environmental concerns are influencing the direction of product development. In the field of sealants, there is a need to develop products which produce very low amounts of volatile leaving materials during the curing process and during the useful life of the cured product. Faced with this problem, the present inventors discovered Products which can be used to reduce the amount of volatile leaving material formed during the curing process and during the useful life of the cured product.

SUMMARY OF THE INVENTION

An object of the present invention is to produce rapid curing room temperature vulcanizable organosiloxane compositions which contain silicon-bonded acetoxy groups and silicon crosslinkers and chain extenders which cure at room temperature while evolving minimal amounts of volatile material as well as, minimal amounts of leachable by-products. This object is accomplished by this invention.

This invention relates to a composition which is storage stable in a package when protected from moisture but cures to a coherent rubbery solid when removed from the package and exposed to moisture comprising an organopolysiloxane composition having a source of silicon-bonded acetoxy radicals and a silicon compound comprising at least one silicon atom to which is bonded at least two heterocyclic Si-N groups having one heterocyclic silicon atom, one nitrogen atom, and three to six ring carbon atoms wherein the nitrogen atom is bonded to the heterocyclic silicon atom, and either the nitrogen atom or the heterocyclic silicon atom is bonded to the silicon atom through a divalent aliphatic hydrocarbon radical.

DETAILED DESCRIPTION OF THE INVENTION

The reduction of the amount of volatile material produced during the curing process of silicone compositions, as well as, during the useful life of the resulting cured products, such as sealants, is accomplished for compositions which contain silicon-bonded acetoxy groups by using a group bonded to a silicon atom which has one hydrolytically unstable bond and a hydrolytically stable, covalent bond attached to the same silicon atom wherein this tether group contains a nitrogen atom which forms a salt with the by-produced acetic acid generated when the silicon-bonded acetoxy group is hydrolyzed during the curing process.

The organopolysiloxane compositions having a source of silicon-bonded acetoxy radicals are well known in the art. For example, the acetoxy-containing organopolysiloxane compositions described in U.S. Pat. No. 3,035,016 to L. Bruner, U.S. Pat. No. 3,077,465 to L. Bruner, and U.S. Pat. No. 3,274,145 to W. Dupree which are hereby incorporated by reference to show the preparation of organopolysiloxane compositions which contain silicon-bonded acetoxy groups and the compositions per se.

The acetoxy-containing organopolysiloxane compositions can be illustrated by compositions comprising the product obtained by mixing a hydroxyl-endblocked polydiorganosiloxane (silanol functional) represented by the following formula $$YO(R_2^1 SiO)_d H$$

where each $R^1$ is a monovalent group selected from the group consisting of a hydrocarbon radical and a halogenated hydrocarbon group, Y is selected from the group consisting of a hydrogen atom and triorganosilyl group of the formula $R_3Si-$ and d has an average value of from 1 to 1,000, and at least one organoacetoxysilane of the formula $$R'_a Si(OCCH_3)_{3-a}$$
$$\quad\quad\;\;\;\overset{O}{\|}$$

in which R' represents a monovalent radical selected from the group consisting of lower alkyl, fluorinated lower alkyl, alkenyl, and aryl, and a has an average value of from 0 to 2 inclusive.

The silanol functional polydiorganosiloxanes preferably have a viscosity of less than 100 Pa.s at 25° C., and the more preferred are those in which the average value of d is from 50 to 700. $R^1$ can be illustrated by a monovalent hydrocarbon radical such as methyl, ethyl, isopropyl, cyclohexyl, vinyl, allyl, cyclopentenyl, and phenyl, and a halogenated monovalent hydrocarbon radical such as 3,3,3-trifluoropropyl. Preferably, $R^1$ is methyl, vinyl, phenyl, or 3,3,3-trifluoropropyl. The polydiorganosiloxane can contain siloxane units illustrated by dimethylsiloxane, phenylmethylsiloxane, 3,3,3-trifluoropropylmethylsiloxane, diphenylsiloxane, and methylvinylsiloxane. The preferred hydroxyl endblocked polydiorganosiloxane are hydroxyl endblocked polydimethylsiloxane and polydimethylsiloxanes being endblocked on one end by a triorganosiloxy group and on the other end by a hydroxyl group. The triorganosiloxy group YO— where Y is the triorganosilyl group is as defined above in which the preferred group is trimethylsilyl, $(CH_3)_3Si-$. The polydiorganosiloxane which have both hydroxyl end groups and triorganosilyl end groups, should have more than 50 percent, preferably more than 75 percent, of the total endgroups as hydroxyls. Acetoxycontaining organopolysiloxane compositions in which the polydiorganosiloxane contains both hydroxyl endgroups and triorganosilyl endgroups are further described by U.S. Pat. No. 3,274,145 to W. DuPree. The amount of the triorganosilyl group can be used to regulate the modulus of cured products, such as sealants. Higher concentrations of triorganosilyl endgroups provide lower modulus cured sealants.

The acetoxysilane can be either a tetraacetoxysilane, an organotriacetoxysilane, a diorganodiacetoxysilane or mixtures thereof. In certain compositions, the acetoxysilane can be a diorganodiacetoxysilane, preferably as a chain extender. R', in the acetoxysilane, can be a lower alkyl such as methyl, ethyl, propyl, isopropyl, butyl, and tertiarybutyl; alkenyl radicals such as vinyl, allyl, or hexenyl, an aryl radical such as phenyl tolyl, or xylyl; an aralkyl radical such as benzyl or betaphenylethyl; and a fluorinated lower alkyl radical such as 3,3,3-trifluoropropyl. The preferred acetoxysilane is an organotriacetoxysilane especially a mixture of methyltriacetoxysilane and ethyltriacetoxysilane. The amount to acetoxysilane is from 0.5 to 15 parts by weight per 100 parts by weight of the silanol functional polydiorganosiloxane, preferably from 3 to 10 parts by weight of acetoxysilane per 100 parts by weight of silanol functional polydiorganosiloxane.

The acetoxy-containing organopolysiloxane compositions can also contain cure-accelerating catalysts, fillers, rheologycontrol additives, pigments, and other additives used in room temperature vulcanizable compositions which do not add a significant amount of volatile material to the composition which may become volatile during the curing process or during the use of the cured composition, such additional ingredients should not be used.

It is often desirable to accelerate the cure of these compositions by the use of catalysts such as the carboxylic acid salts of metals ranging from lead to manganese inclusive in the electromotive series of metals as disclosed in U.S. Pat. No. 3,077,465 by Bruner. Other silanol condensation catalysts can also be used such as stannous carboxylates, for example stannous octoate, and titanates such as tetrabutyltitanate, tetraisopropyltitanate, and bis(ethoxyacetoacetonate)diisopropoxy titanium (IV). The preferred curing catalysts are dibutyltin diacetate, dibutyltin dilaurate, tetrabutyl titanate, tetraisopropyl titanate, bis(ethoxyacetoacetonate)diisopropoxy titanium (IV), and stannous octoate.

Fillers can be used in room temperature vulcanizable organosiloxane compositions of this invention. These fillers include reinforcing silica fillers, both treated and untreated including fume silica, silica aerogel, silica zerogel, and precipitated silicas; extending fillers including crushed quartz, aluminum oxide, magnesium oxide, calcium carbonate, zinc oxide, talc, diatomaceous earth, iron oxide, clays, titanium dioxide, zirconia, sand, carbon black, and graphite. The preferred fillers are reinforcing silica, treated reinforcing silica, calcium carbonate, and carbon black.

The compositions of this invention can also contain a chain extender other than the diorganodiacetoxysilane. Such a chain extender can be an amide such as bis(N-methylacetamido)methylvinylsilane.

The compositions of the present invention contain a silicon compound comprising at least one silicon atom to which is bonded at least two heterocyclic Si-N groups having one heterocyclic silicon atom, one nitrogen atom, and three to six ring carbon atoms wherein the nitrogen atom is bonded to the heterocyclic silicon atom and either a nitrogen atom or the heterocyclic silicon atom is bonded to the silicon atom through a divalent saturated aliphatic hydrocarbon radical. These silicon compounds are azasilacycloalkanes.

These azasilacycloalkanes are silicon compounds which are stable at room temperature when protected from moisture, but polymerize when exposed to moisture in such a manner that no volatile or leachable by-products are produced. They polymerize via a water induced ring opening reaction which yields a silanol. This silanol can either open another ring, creating a siloxane linkage; or condense with another silanol, resulting in a siloxane linkage and a molecule of water. The group bound to a silicon atom which is displaced by the water is "tethered" to the central silicon atom via a bridge of covalently bonded atoms attached to the same silicon atom. What is meant by tethered is that all of the covalent bonds of the bridging chain are relatively stable to hydrolysis when compared to the silicon hydrolyzable bond.

It is the azasilacycloalkanes which provide the compositions of this invention to have a low amount of volatile material given off during the curing process. This is because the azasilacycloalkane group when hydrolyzed does not produce a leaving material, but instead remains tethered to the base polymer. Also, the group resulting from the hydrolysis of the azasilacycloalkane forms a salt with the by-produced acetic acid and this further keeps the amount of volatile material to a minimum.

The azasilacycloalkanes used in the compositions of the present invention are crosslinkers and optionally chain extenders. The crosslinkers have at least three heterocyclic Si—N groups (azasilacycloalkane groups) per molecule. The chain extenders have two azasilacycloalkane groups per molecule. Preferred azasilacycloalkane groups have three ring carbon atoms, i.e. azasilacyclopentane groups are illustrated by the following formulae

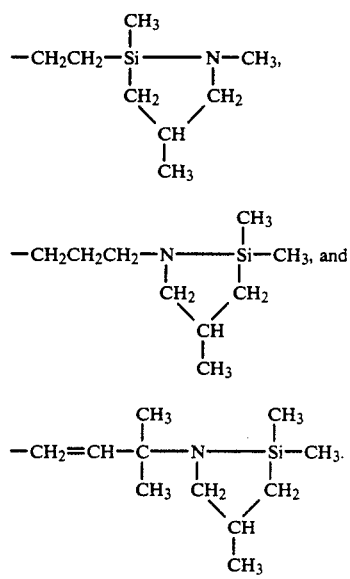

These azasilacyclopentane groups are bonded to silicon atoms of polyorganosiloxanes.

Azasilacycloalkane crosslinkers can be illustrated by the following formulae in which Z is an azasilacycloalkane group as defined above

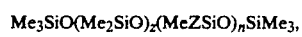

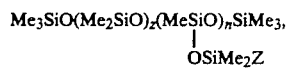

and

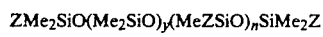

where each Z is an azasilacycloalkane group or a hydrogen atom where the number of azasilacycloalkane groups per molecule is greater than 2, R is a monovalent hydrocarbon radical, z is an integer of from 3 to 10, y is $\geq 0$, and n is $\geq 3$.

Azasilacycloalkane chain extenders can be illustrated by the following formulae in which Z is one of the azasilacycloalkanes defined above, ZMe$_2$SiO(Me$_2$SiO)$_y$SiMe$_2$Z, ZMe$_2$Si-X-SiMe$_2$Z, and

where Z is an azasilacycloalkane group as previously illustrated, R is a monovalent hydrocarbon group, X is a divalent hydrocarbon radical selected from the group consisting of —(CR$_2$)$_m$— or —C$_6$H$_4$—, y is $\geq 0$, and m is 2 to 6 inclusive.

The azasilacycloalkanes, whether chain extender or crosslinker, can be made by reacting silicon compounds having silicon-bonded hydrogen atoms with aliphatically unsaturated azasilacycloalkanes in the presence of a platinum catalyst. This reaction produces the heterocyclic Si—N groups which are the azasilacycloalkanes bonded to the silicon compounds.

The aliphatically unsaturated azasilacyclopentanes react with the silicon compounds having Si—H groups in the presence of a platinum catalyst. The reaction resulting from this combination is termed an "addition reaction" and a "hydrosilylation reaction" where the aliphatic unsaturation reacts with the silicon-bonded hydrogen such that the Si—H adds across the double bond. Platinum catalysts are well know in the art for catalyzing this reaction. These platinum catalysts include the chloroplatinic acid described by Speier et al in U.S. Pat. No. 2,823,218, issued Feb. 11, 1958; complexes of chloroplatinic acid with low molecular weight vinyl-containing polydiorganosiloxanes such as syn-divinyl-tetramethyldisiloxane as described by Willing in U.S. Pat. No. 3,417,593, issued Dec. 31, 1968; alkene complexes described by Ashby i U.S. Pat. No. 3,159,601, issued Dec. 1, 1964, and U.S. Pat. No. 3,159,662, issued Dec. 1, 1964; the platinum acetylacetonate described by Baney in U.S. Pat. No. 3,723,497, issued Mar. 27, 1973; the platinum alcoholates described by Lamoreaux in U.S. Pat. No. 3,220,972, issued Nov. 30, 1965; and in many more patents which describe various types of platinum catalysts. These patents describing platinum catalysts are hereby incorporated by reference to show the platinum catalysts and to show the hydrosilylation reaction.

The aliphatic unsaturated azasilacycloalkanes can be illustrated by the preferred azasilacyclopentanes having the general formula

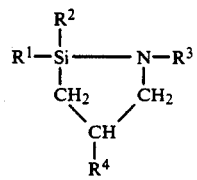

in which each of R$^1$, R$^2$, R$^3$, and R$^4$ is independently selected from the group consisting of a hydrogen atom and a monovalent hydrocarbon radical, where one of R$^1$, R$^2$, and R$^3$ is a monovalent hydrocarbon radical with olefinic unsaturation or acetylenic unsaturation. The monovalent hydrocarbon radicals include methyl, ethyl, propyl, butyl, phenyl, vinyl, allyl, hexenyl, cyclohexyl, tolyl, and isopropyl. Preferably, R$^1$, R$^2$, or R$^3$, when an olefinically or acetylenically unsaturated monovalent hydrocarbon radical, is olefinic and either vinyl, allyl, or hexenyl.

The aliphatically unsaturated azasilacyclopentanes can be prepared from an dialkoxy(chloroalkyl)silane of the general formula $$(R^5O)_2SiCH_2CHCH_2Cl \quad \text{(I)}$$
(with R$^2$, R$^4$ substituents)

where R$^5$ is an alkyl radical of from 1 to 5 carbon atoms per molecule, including methyl, ethyl, propyl, isopropyl, butyl, isobutyl, and pentyl, by first making a monoalkoxyalkylalkenyl(3-chloro-2-alkylpropyl)silane of the general formula $$(R^5O)SiCH_2CHCH_2Cl \quad \text{(II)}$$
(with R$^2$, R$^4$, R$^1$ substituents)

by reacting silane (I) with a Grignard reagent of the general formula R$^1$MgX, where X is chlorine, bromine, or iodine, or LiX reagent in the presence of an ether such as diether ether, tetrahydrofuran, or a mixture thereof. One preferred monoalkoxyalkylalkenyl(3-chloro-2-alkylpropyl)silane is methoxymethylvinyl(3-chloro-2-methylpropyl)silane. After the silane (II) is obtained, it can be reacted with acetyl chloride in the presence of a Lewis acid, preferably ferric chloride to make a chloroalkylalkenyl(3-chloro-2-alkylpropyl)silane of the general formula $$ClSiCH_2CHCH_2Cl. \quad \text{(III)}$$
(with R$^2$, R$^4$, R$^1$ substituents)

One preferred chloroalkylalkenyl(3-chloro-Z-alkylpropyl)silane is chloromethylvinyl(3-chloro-2-methylpropyl)silane.

These aliphatically unsaturated azasilacyclopentanes can be made by a process described by Speier in U.S Pat. No. 3,146,250, issued Aug. 25,1964, where a halogenoalkylhalogenosilane of the formula

is reacted with an amino compound of the formula RNH$_2$, for example, the aliphatically unsaturated azasilacyclopentanes can be made by reacting an alkenylamine with a silane of formula (III). Speier is hereby incorporated by reference to show the known general reaction of chlorosilanes with an amino compound to make certain nitrogen-containing compounds as described herein.

The above aliphatically unsaturated azasilacyclopentanes are reacted with silicon-bonded hydrogen containing compounds in the presence of a platinum catalyst, preferably with heating. The silicon-bonded hydrogen containing compounds can be illustrated by the following HMe$_2$SiOSiMe$_2$H, (MeHSiO)$_4$, (MeHSiO)$_5$, HMe$_2$SiO(Me$_2$SiO)$_{98}$SiMe$_2$H, Me$_3$SiO(Me$_2$SiO)$_3$-(MeHSiO)$_5$SiMe$_3$, (HMe$_2$SiO)$_3$SiMe, (HMe$_2$SiO)$_4$Si, ((HMe$_2$SiO)$_3$SiO$_{178}$)$_2$((HMe$_2$SiO)$_2$SiO)$_4$, and (HSiO$_{3/2}$)$_{12}$, in which Me is methyl.

A chain extender may be prepared as follows:

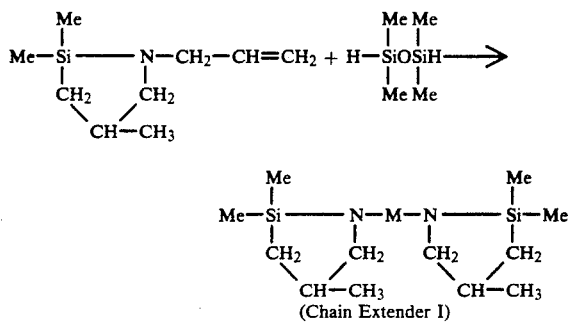

(reaction is carried out in the presence of a platinum catalyst and $M = -CH_2CH_2CH_2-\underset{\underset{Me}{|}}{\overset{\overset{Me}{|}}{Si}}-O-\underset{\underset{Me}{|}}{\overset{\overset{Me}{|}}{Si}}-CH_2CH_2CH_2-)$ Chain Extender I + HO$-$(SiO)$_d$$-$H $\longrightarrow$
            |
            Me

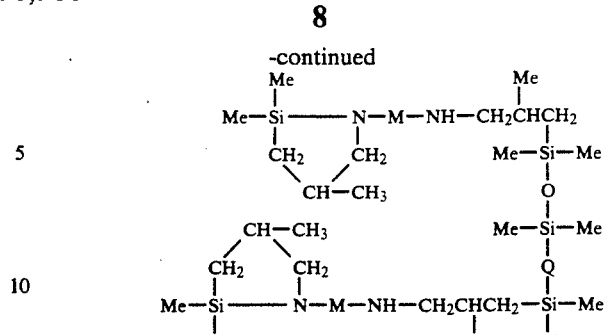

($d$ is an average value of at least one and Q is $-(Me_2SiO)_{(d-1)}-$)

The above chain extending reaction can react further as long as there are heterocyclic Si—N groups and silanols available. This chain extending reaction can take place in the presence of crosslinking reactions. From the above illustration, there are no volatile compounds produced.

An example of a crosslinker, which is reacted with a hydroxyl endblocked polydimethylsiloxane, is prepared as follows:

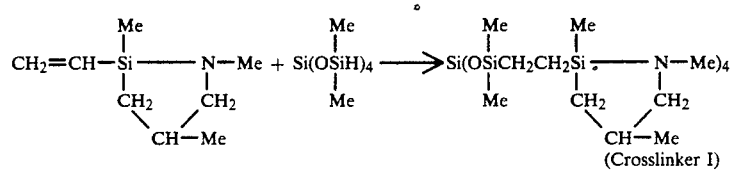

(This reaction takes place in the presence of a platinum catalyst)

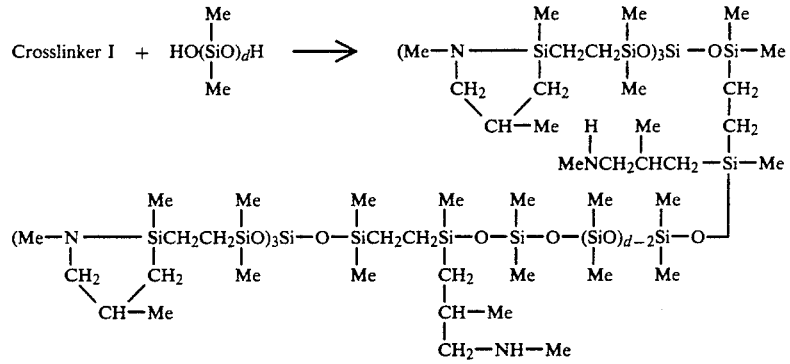

These crosslinkers can further react with moisture or other silanol functionality to cure compositions. By using combinations of crosslinkers and chain extenders one can vary the resulting properties of the cured product. Additionally, the cure properties can be varied by the nature of the silanol functional polysiloxanes which are used.

The heterocyclic Si—N groups of the chain extenders and crosslinkers are believed to react in the following manners:

(1) with water

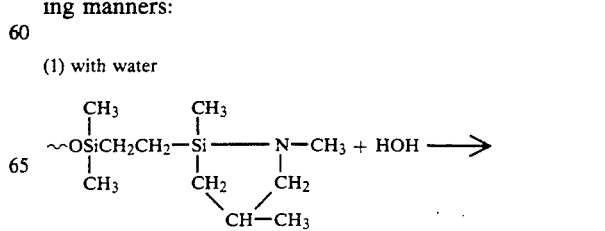

-continued

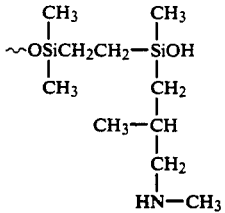

or,

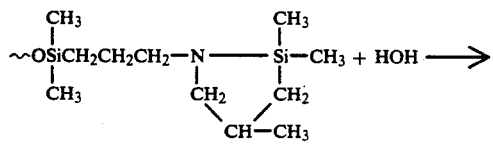

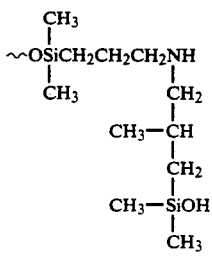

(2) with silanol, ≡Si—OH

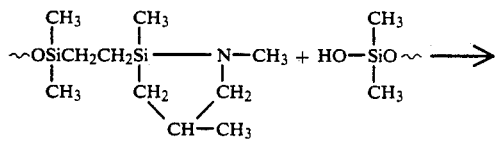

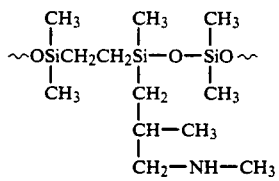

or

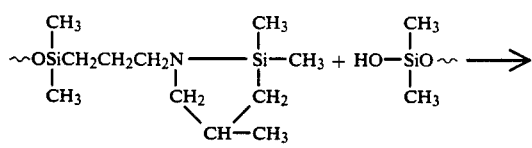

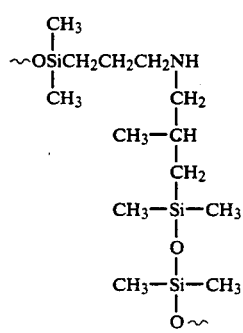

The above reactions are illustrative only using preferred heterocyclic Si—N groups.

The compositions, which are storage stable in a package when protected from moisture but polymerize and cure when removed from the package and are exposed to moisture of the atmosphere, can be made by mixing azasilacycloalkane crosslinkers (as described herein) with acetoxysilane crosslinkers, and polyorganosiloxanes having silicon-bonded hydroxyl groups (silanols, Si—OH) or by mixing azasilacycloalkane crosslinkers and azasilacycloalkane chain extenders (as described herein) with acetoxy silane crosslinkers and polyorganosiloxanes having SiOH groups. These compositions can contain fillers and other ingredients which are useful in the preparation of sealants. Fillers which may be useful are illustrated by reinforcing silica, surface treated reinforcing silica, calcium carbonate, and carbon black. Curing catalysts which might be useful are illustrated by dibutyltin diacetate, dibutyltin dilaurate, tetrabutyl titanate, tetraisopropyl titanate, stannous octoate, and bis(ethoxyacetoacetonate)diisopropoxy titanium (IV).

The compositions of the present invention are storage stable in one package when protected from moisture but polymerize and cure when removed from the package and exposed to moisture of the atmosphere. These compositions can be made by mixing (A) crosslinkers of the present invention having a formula selected from the group consisting of

$Si(OSiMe_2Z)_4$, $RSi(OSiMe_2Z)_3$, 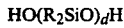$(MeZSiO)_x$ ⏋, $Me_3SiO(Me_2SiO)_x(MeZSiO)_nSiMe_3$,

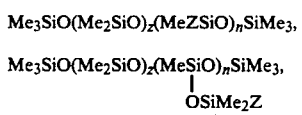

and

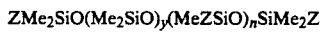

$ZMe_2SiO(Me_2SiO)_y(MeZSiO)_nSiMe_2Z$ where each Z is an azasilacycloalkane group or a hydrogen atom where the number of azasilacycloalkane group per molecule is greater than 2, R is a monovalent hydrocarbon radical, z is an integer of from 3 to 10, y is $\geq 0$, and n is $\geq 3$ with (B) a silanol functional siloxane selected from the group consisting of a linear polydiorganosiloxane represented by the following formula $HO(R_2SiO)_dH$ where R is a monovalent hydrocarbon radical, such as methyl, ethyl, propyl, hexyl, vinyl, phenyl, and 3,3,3-trifluoropropyl and d has an average value of from 1 to 1,000; and (C) a silicon compound containing silicon-bonded acetoxy radicals. The molar ratio of the heterocyclic Si—N group plus acetoxy radical per silanol group (Si—OH) is in the range of 2:1 to 50:1.

The compositions of this invention are stable when stored in containers which protect them from exposure to moisture, but cure rapidly when exposed to moisture. The cure is very rapid, for example, at room temperature and 44% relative humidity, the cure can be considered instantaneous and at 2% relative humidity, the cure occurs in 30 seconds. Cured compositions were observed to have water contact angles of about 50°. Cured sealants can be painted with latex paints.

The following syntheses and example are presented for illustrative purposes and should not be construed as limiting the invention which is properly delineated in the claims. In the following examples, "part" and "parts" are respectively "part by weight" and "parts by weight", Me=methyl, Ph=phenyl, and Vi=vinyl.

SYNTHESIS 1

Reaction of 1,1,3,3-tetramethyldisiloxane with 1,2,4-trimethyl-1-vinyl-2-aza-silacyclopentane.

The 1,2,4-trimethyl-1-vinyl-2-aza-silacyclopentane was prepared as follows. To a solution of 50.0 g (254 mmol) of dimethoxy-methyl(3-chloro-2-methylpropyl)-silane in 250 ml of diethyl ether in a three-necked, 1 L (liter) round-bottom flask fitted with a mechanical stirrer, nitrogen inlet, and addition funnel was added over a one hour period, a solution of 290 ml(290 mmol) of 1M (molar) vinyl magnesium bromide in tetrahydrofuran (THF). The reaction was allowed to stir overnight under a nitrogen atmosphere at room temperature and the slightly yellowish liquid was decanted from the solids. The solvents were removed at 40° C. and 9 mmHg to yield 68.09 g of a yellow liquid with considerable amounts of solids. To this was added 50 ml of benzene and the salts were removed by filtration through a course glass frit funnel. The collected solids were washed with two 30 ml portions of benzene. The combined organic fractions were stripped at 50° C. and 9 mmHg to yield 40.19 g of liquid with a small amount of salts. The results of gas chromatography-mass spectroscopy (GC-MS) showed the following composition of the liquid:

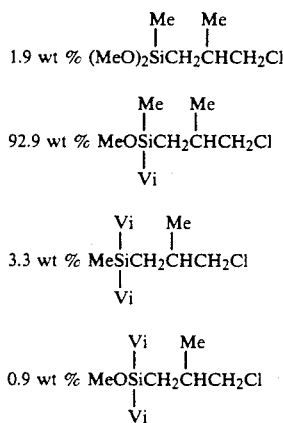

3.1 wt % of 9 unidentified impurities at an order of magnitude lower level.

The mass spectra was used to identify these compounds and the results were:

For B compound: 192, not observed, M+; 165(10), M-Vi; 137 (10),NA; 121(210), (MeO)ViClSi+; 109(230), (MeO)MeClSi+; 101(780), (MeO)MeViSi+; 56(1000), $C_4H_8^+$ where data are presented as charge (m/e), (relative intensity).

For C compound: 188, not observed, M+; 161(8), M-Vi; 117 (280), $Vi_2ClSi^+$; 105(284), MeViSi+; 97(489), $Vi_2MeSi^+$; 56(1000), $C_4H_8^+$.

For D compound: 204, not observed, M+; 177(10), M-Vi; 121 (290), (MeO)ViClSi+; 113(620), (MeO)-$Vi_2Si^+$; 56(1000), $C_4H_8^+$.

The $^{29}Si$ nuclear magnetic resonance(NMR) had one major peak at 6.63 ppm relative to tetramethylsilane. The crude product was purified by short path distillation. The fraction boiling at 75° C. at 6 mmHg weighed 28.22 g (58% yield) and was identified as compound B, methoxymethylvinyl(3-chloro-2-methylpropyl)silane.

Chloromethylvinyl(3-chloro-2-methylpropyl)silane was prepared as follows. A mixture of 28.00 g (143.3 mmol) of compound B in 15.5 ml (17.10 g, 217.9 mmol, 1.5 eq) of acetyl chloride was allowed to sit at ambient temperature for 12 hours. A slight exotherm was noted. The low boiling material was removed by distillation and the product distilled at 88° C. to 90.5° C. and 30 mmHg to give 25.2 g of material (88% yield). The product was chloromethylvinyl(3-chloro-2-methylpropyl)silane as was identified by $^{13}C$ NMR: 134.79 and 134.73 and 134.68 (1:2:1, 1.67), SiVi; 52.93 (1.00), $CH_2Cl$; 31.51 and 31.48 (0.83), CH; 22.88 and 22.84 (0.97), CHMe; 20.13 and 20.10 (1.01), $SiCH_2$; 0.59 and 0.54 (0.68), SiMe and by $^{29}Si$ NMR: 17.81 and 17.78 (1:1) where data are presented as ppm (relative intensity).

Methylamine was condensed into a 1 L round-bottom flask and distilled from sodium. To 490 ml (340 g, 11 mol) of methylamine was slowly added 309.8 g (1.57 mol) of chloromethylvinyl(3-chloro-2-methylpropyl)silane, which resulted in two phases. The two phase system was transferred to a Parr reactor and heated at 110° C. and 230 psig for 10 hours. The reaction mixture was cooled to −10° C., transferred to a 2 L round-bottom flask and 400 ml of cold pentane was added. The layers were separated, and the upper organic phase concentrated. After concentration, some ammonium salts had precipitated. These salts were removed by filtration and the product purified by distillation at reduced pressure to yield about 160 g (60% yield) of aza-silacyclopentane with a small amount of ammonium salts. The distilled product was 97% pure 1,2,4-trimethyl-1-vinyl-2-azasilacyclopentane with two major higher boiling impurities (about 1 wt % each) and numerous minor higher boiling impurities. The GC MS data was: 1,2,4-Trimethyl-1-vinyl-2-azasilacyclopentane, Retention Time 2.00 min; 155 (365), M+; 154 (243), M+-H; 140(97), M+-Me; 126 (113), M+-Vi; 113 (962, M+-$C_3H_7$; 112 (1000), M+; 89 (396), MeViSiN=$CH_2^+$; 71 (465) MeViSiH+. The $^{13}C$ NMR spectra was: 138.23 and 137.98. terminal vinyl; 132.86 and 137.98, internal vinyl; 62.19 and 61.92, $NCH_2$; 33.93 and 33.80, methine; 32.09 and 32.06, NMe; 21.48 and 21.54, CHMe; 21.23 and 20.95 Si-$CH_2$; −3.43 and −4.29, SiMe. The $^{29}Si$ NMR had peaks at 6.229 and 6.039 relative to tetramethylsilane.

SYNTHESIS 2

Reaction of Tetrakis(dimethylsiloxy)silane with 1,2,4-Trimethyl-1-vinyl-2-aza-silacyclopentane A flask fitted with an addition funnel containing 1,2,4-trimethyl-1-vinyl-2-aza-silacyclopentane, as prepared in Synthesis 1, was charged with tetrakis(dimethylsiloxy)silane and a platinum catalyst of the formula

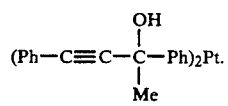

The mole ratio of the azasilacyclopentane to tetrakis(-dimethylsiloxy)silane was about 4 to 1. The mixture was warmed to about 120° C. IR indicated some residual SiH. A vacuum distillation head was attached and the product stripped until no volatiles were evolved at 170° C. and 0.04 mmHg. The product was an azasilacyclopentane functional crosslinker which had the following average formula where the sum of the subscripts equals four for any given compound:

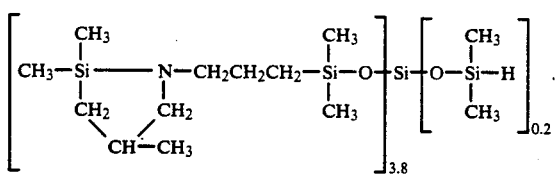

EXAMPLE

A room temperature vulcanizable silicone sealant was prepared by mixing in a container which protected it from exposure to moisture, as the organopolysiloxane composition having a source of silicon-bonded acetoxy radicals, 85 parts of a polydimethylsiloxane having about 85 percent silicon-bonded hydroxyl endgroups and about 15 percent trimethylsiloxy endgroups and an average molecular weight of about 40,000, 11 parts of reinforcing silica filler, 2 part of methyltriacetoxysilane, 2 parts of ethyltriacetoxysilane, and about 0.02 parts of dibutyltindiacetate; and 14.26 parts of the azasilacyclopentane functional crosslinker as prepared in Synthesis 2. The resulting mixture was blended for 10 minutes and then the entrapped air was removed by centrifuge. A portion of the resulting mixture was extruded from the container into an atmosphere which was at ambient laboratory temperature and 44% relative humidity. The mixture skinned over instantaneously. Another portion of the resulting mixture was extruded from the tube into an atmosphere which was at ambient laboratory temperature and 2% relative humidity. Under these conditions the sealant skinned over in 30 seconds. Very little odor of acetic acid was detected by nose during the curing process. After three days, the physical properties of the resulting coherent rubbery solid were determined and were:

Tensile strength at break = 186 psi

Elongation at break = 479%

Young's Modulus = 68.5 psi

100% Modulus = 50.9 psi

200% Modulus = 88.0 Psi

Water Contact Angle = 50 degrees

The surface of the cured sealant was easily painted using a commercial water based latex paint.

That which is claimed is:

1. A composition comprising a product which is storage stable in a package when protected from moisture but cures to a coherent rubbery solid when removed from the package and exposed to moisture comprising an organopolysiloxane composition having a source of silicon-bonded acetoxy radicals and a silicon compound comprising at least one silicon atom to which is bonded at least two heterocyclic Si—N groups having one heterocyclic silicon atom, one nitrogen atom, and three to six ring carbon atoms wherein the nitrogen atom is bonded to the heterocyclic silicon atom, and either a nitrogen atom or the heterocyclic silicon atom is bonded to the silicon atom through a divalent aliphatic hydrocarbon radical.

2. The composition according to claim 1 in which the heterocyclic Si—N groups are azasilacyclopentane groups.

3. The composition according to claim 2 in which the azasilacyclopentane groups of the silicon compound are selected from the group consisting of

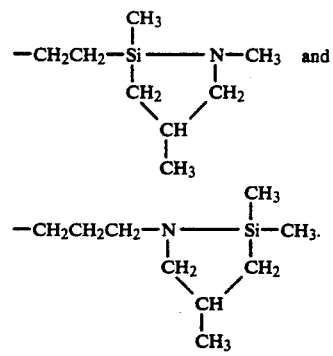

4. The composition according to claim 3 in which the silicon compound has at least three azasilacyclopentane groups per molecule.

5. The composition according to claim 4 in which the product is obtained from mixing (A) crosslinkers having a formula selected from the group consisting of

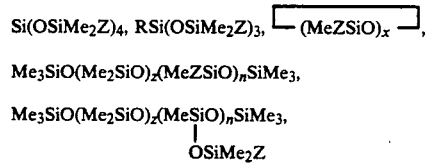

$Me_3SiO(Me_2SiO)_z(MeZSiO)_nSiMe_3$, $Me_3SiO(Me_2SiO)_z(MeSiO)_nSiMe_3$,
        |
        $OSiMe_2Z$ and $ZMe_2SiO(Me_2SiO)_y(MeZSiO)_nSiMe_2Z$ where each Z is an azasilacyclopentane group or a hydrogen atom where the number of azasilacyclopentane groups per molecule is greater than 2, R is a monavalent hydrocarbon radical, z is an integer of from 3 to 10, y is $\geq 0$, and n is $\geq 3$, (B) a silanol functional polydiorganosiloxane represented by the following formula $HO(R_2^1SiO)_dH$ where $R^1$ is a monovalent hydrocarbon radical, and d has an average value of from 1 to 1,000, and (C) at least one organoacetoxysilane of the formula

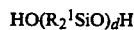

in which R' represents a monovalent radical selected from the group consisting of lower alkyl, fluorinated lower alkyl, alkenyl, and aryl, and a has an average value of from 0 to 2 inclusive.

6. The composition according to claim 5 in which the product further comprises a chain extender selected from the group consisting of $ZMe_2SiO(Me_2SiO)_ySiMe_2Z$, $ZMe_2Si\text{-}X\text{-}SiMe_2Z$, and

where Z is an azasilacyclopentane group, R is a monovalent hydrocarbon group, X is a divalent hydrocarbon radical selected from the group consisting of —(CR$_2$)$_m$— or —C$_6$H$_4$—, y is $\geq 0$, and m is 2 to 6 inclusive.

7. The composition according to claim 1 further comprising a condensation catalyst.

8. The composition according to claim 2 further comprising a condensation catalyst.

9. The composition according to claim 8 in which the condensation catalyst is a compound selected from the group consisting of dibutyltin diacetate, dibutyltin dilaurate, tetrabutyl titanate, tetraisopropyl titanate, bis(ethoxyacetoacetonate)diisopropoxy titanium (IV), and stannous octoate.

10. The composition according to claim 8 further comprising a filler.

11. The composition according to claim 9 further comprising a filler.

12. The composition according to claim 10 in which the filler is selected from the group consisting of reinforcing silica, treated reinforcing silica, calcium carbonate, and carbon black.

13. The composition according to claim 11 in which the filler is selected from the group consisting of reinforcing silica, treated reinforcing silica, calcium carbonate, and carbon black.

14. The composition according to claim 3 further comprising a condensation catalyst.

15. The composition according to claim 14 in which the condensation catalyst is a compound selected from the group consisting of dibutyltin diacetate, dibutyltin dilaurate, tetrabutyl titanate, tetraisopropyl titanate, bis(ethoxyacetoacetonate)diisopropoxy titanium (IV), and stannous octoate.

16. The composition according to claim 14 further comprising a filler.

17. The composition according to claim 15 further comprising a filler.

18. The composition according to claim 16 in which the filler is selected from the group consisting of reinforcing silica, treated reinforcing silica, calcium carbonate, and carbon black.

19. The composition according to claim 17 in which the filler is selected from a group consisting of reinforcing silica, treated reinforcing silica, calcium carbonate, and carbon black.

20. The composition according to claim 5 further comprising a condensation catalyst.

21. The composition according to claim 20 in which the condensation catalyst is a compound selected from the group consisting of dibutyltin diacetate, dibutyltin dilaurate, tetrabutyl titanate, tetraisopropyl titanate, bis(ethoxyacetoacetonate)diisopropoxy titanium (IV), and stannous octoate.

22. The composition according to claim 20 further comprising a filler.

23. The composition according to claim 21 further comprising a filler.

24. The composition according to claim 23 in which the filler is selected from the group consisting of reinforcing silica, treated reinforcing silica, calcium carbonate, and carbon black.

25. The composition according to claim 23 in which the filler is selected from the group consisting of reinforcing silica, treated reinforcing silica, calcium carbonate, and carbon black.

* * * * *